United States Patent [19]

Solomon

[11] 4,337,364

[45] Jun. 29, 1982

[54] OLEFIN OXIDATION WITH SUPPORTED CUO CATALYST

[75] Inventor: Paul W. Solomon, Bartlesville, Okla.

[73] Assignee: Phillips Petroleum Company, Bartlesville, Okla.

[21] Appl. No.: 228,037

[22] Filed: Jan. 23, 1981

[51] Int. Cl.³ .................... C07C 45/35; C07C 47/20
[52] U.S. Cl. .................................. 568/475; 568/476
[58] Field of Search ................. 568/475, 477, 476

[56] References Cited

U.S. PATENT DOCUMENTS

| | | | |
|---|---|---|---|
| 2,066,622 | 1/1937 | Hasche | 568/475 |
| 2,503,291 | 4/1950 | Odell | 568/475 |
| 2,627,527 | 2/1953 | Connolly et al. | 260/604 |
| 2,807,647 | 9/1957 | Cheney et al. | 568/475 |
| 2,990,427 | 6/1961 | Cadwell | 568/475 |
| 3,209,034 | 9/1965 | Narita et al. | 260/604 |
| 4,155,938 | 5/1979 | Yamamoto et al. | 260/604 |

OTHER PUBLICATIONS

Kirk–Othmer, "Ency. of Chem. Tech.", vol. 1, 2nd Ed., p. 266 Jun., 1963.

Primary Examiner—Werren B. Lone

[57] ABSTRACT

A method for producing catalyst by impregnating a support with an aqueous solution of CuO, drying the impregnated support at about 90° C. to about 150° C. to provide a powdery product support impregnated with about 0.1 to about 5 weight percent CuO. A method for preparing aldehydes from olefins in the presence of an oxygen containing gas and a catalyst as prepared above.

4 Claims, No Drawings

OLEFIN OXIDATION WITH SUPPORTED CUO CATALYST

BACKGROUND OF THE INVENTION

This invention relates to catalyst preparation. In one of its aspects it relates to olefin oxidation. In another aspect it relates to CuO containing catalyst.

Acrolein and methacrolein are valuable starting materials for the synthesis of chemicals useful in textile finishings, paper treating and the manufacture of rubber chemicals, pharmaceuticals, plasticizers and synthetic resins. One of the largest single uses for acrolein has been in the production of the amino acid methionine. Acrolein and methacrolein can be prepared commercially by the oxidation of propylene and isobuylene respectively using various type catalysts such as cuprous oxide, mixed oxides of bismuth, molybdenum and cobalt, oxides of antimony plus other metals, or combinations including tungsten oxide and silver selenide. Of this group supported cuprous oxide, $Cu_2O$, seems to be the only catalyst used commercially.

Cupric oxide, CuO, prepared by other processes is known to be used by itself or in combination with other metal catalysts as a catalyst for the oxidation of propylene to acrolein although the conversions and product selectivities are generally lower than those of the instant invention. In addition to the catalyst preparation the concentrations used in known CuO catalyzed reactions are different than the instant invention. It is believed that both the manner of preparation and catalyst concentration are contributing factors in the improved conversion and selectivity for olefin oxidation described herein. The essence of the instant invention is to employ a catalyst for the oxidation of olefins to aldehydes that is a supported cupric oxide catalyst prepared by a process other than the calcining process well known in the prior art.

It is therefore an object of this invention to provide a method for preparing a supported CuO catalyst. It is another object of this invention to provide a catalyst and method for preparing aldehyde from olefins.

Other aspects, objects and the various advantages of this invention will become apparent upon study of this specification and the appended claims.

STATEMENT OF THE INVENTION

According to this invention a method is provided for preparing a catalyst in which a support is impregnated with an aqueous solution of cupric oxide, the impregnated support is dried to powder at a temperature in the range of about 90° C. to about 150° C., to produce a support impregnated with about 0.1 to about 5 weight percent cupric oxide.

In a further embodiment of the invention a catalyst prepared as described above is employed in the oxidation of olefin to aldehyde.

Olefins useful in this invention are those materials represented by the formula

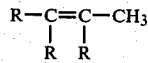

wherein each R can be hydrogen or any alkyl group having from one to eight carbon atoms and each R can be the same or different from the other R's. Exemplary of such materials are: propylene, 2-methylpropene (isobutylene), 2-butene, 2-methyl-2-butene, 2,3-demethyl-2-butene, 2-methyl-1-butene, 2-methyl-1-octene, 2-methyl-1-decene, 2-ethyl-2-hexene, and the like and mixtures thereof. Propylene and isobutylene are the preferred olefinic hydrocarbons to be used since other olefinic hydrocarbons tend to produce some ketones in addition to unsaturated aldehydes.

The catalyst useful in this invention is cupric oxide, CuO, on any suitable support. Any common catalyst support can be used in this invention such as α-alumina (α-$Al_2O_3$), magnesia, asbestos, carbon, zinc aluminate, silica gel and the like. The concentration of CuO on a support considered useful in this invention is, broadly, 0.1 to 5 wt. percent, preferably, 0.5 to 2.5 wt. percent of the total wt. of CuO and support.

The catalyst can be prepared by any known method such as, for example, precipitation of a cupric salt (e.g. $CuCl_2$) with a base followed by mulling. Mulling is defined as the removal of water (drying) from an aqueous cupric oxide suspension with or without support present under mild temperature conditions such as 90°–150° C. as opposed to the usual calcining technique which generally involves heating the cupric salt at temperatures elevated above 350° C.

Generally air is used as the oxidant in the preparation of aldehydes according to this invention although any other oxygen-containing gas, as well as pure oxygen, can also be used. When air is used, the mole ratio of air to olefin is generally between about 20:1 to about 1:1. The reaction temperature is generally in the range of about 350° C. to 500° C. The reaction pressure can be from 0 to 200 psig. The process is not dependent upon any particular method of recovery of the useful products of oxidation. The product may be recovered by chilling the reaction products and fractionating the desired unsaturated aldehyde by distillation.

The following examples serve to illustrate the operability of this invention.

EXAMPLE I

This example describes the preparation of the control catalyst, referred to herein as calcined catalyst, and the inventive catalyst, referred to herein as mulled catalyst. The calcined catalyst was prepared as follows: To 20 milliliters of hot (50°–80° C.) concentrated nitric acid was added 5 grams of $Cu(NO_3)_2 \cdot 2\frac{1}{2}H_2O$ and 20 grams of α-alumina and the mixture stirred for a few minutes partially to dissolve the copper salt. The mixture was heated on a steam bath (90°–95° C.) to remove nitric acid. The mixture was then heated (calcined) at 400° C. for one hour, cooled, 10 milliliters of water added and the mixture dried on a steam bath and again calcined at 400° C. for one hour to give 26.7 grams of a product estimated to have 1.76 grams (6.6 wt. %) CuO. The product was considered to be an active catalyst.

The inventive mulled catalyst was prepared as follows: To a small beaker was added 4 grams of pure CuO (Alfa Chemical Co.), 20 grams of α-alumina and 10 milliliters of water and the mixture heated on a steam bath to remove most of the water, the final drying being done at 120° C. in oven for one hour to give a gray to black powder. The dry powder was sieved using a U.S. Standard Sieve screen size 100 mesh. About 3.8 grams of black powder passed through which was assumed to be pure CuO. It was thereby determined that the α-alumina (20 grams) had 0.2 grams CuO deposited on the surface which was calculated to be a catalyst level of 1 wt. % CuO. This "mulled" product was considered to be an active catalyst.

EXAMPLE II

This example illustrates the invention using the inventive mulled CuO/βAl$_2$O$_3$ catalyst and describes the apparatus and procedures used to carry out both the inventive and the control runs. The entire metal reactor system described herein was precleaned by heating in 35 wt. % HNO$_3$, washing with H$_2$O, 5 wt. % aqueous NaHCO$_3$, H$_2$O and acetone, allowing to stand two hours in 2 wt. % aqueous tetrasodium ethylenediamine tetraacetate washing with H$_2$O, acetone, and air drying. All glass liners and thermowells were kept in the last mentioned solution until ready to use when they were rinsed and air dried. The liners and thermowells were discarded after only one use to avoid any possibility of contamination from run to run.

The reactor used in all work consisted of a vertical 14 inches × 0.5 inch 316 stainless steel tube lined with a 0.5 inch removable glass liner which was sealed at the bottom except for several holes of about 1 mm diameter to allow for gas passage. A 3 mm glass thermowell extended down the center of the reactor and allowed a sliding thermocouple to be positioned anywhere in the reactor. The glass liner was press-sealed to the reactor at the top with a thin 97 wt. % pure asbestos paper wrapping. The thermowell was sealed into the 316 stainless steel head using Teflon ® polymer ferrules. The associated feed system consisted of appropriate gas cylinders feeding through rotometers into a manifold which was attached to a 2 inch × 0.25 inch fitting packed with small quartz chips for gas mixing and then to the head of the reactor. All lines were 316 stainless steel. Two ports for sampling of gases by GLC analysis were provided, one in the line just ahead of the reactor head and one at the reactor outlet. The reactor head contained a pressure gauge and valves to regulate gas flows. The entire apparatus was heated with electrical heating tape.

To the reactor described was charged 9.55 grams (5 milliliters) of the inventive mulled CuO/α-Al$_2$O$_3$ catalyst described in Example I. While the reactor was being slowly heated to reaction temperature (above 200° C.) air (191 milliliters per minute STP), and propylene (9.3 milliliters per minute, STP) were passed downwardly through the catalyst bed at a 2400 Gas Hourly Space Velocity (GHSV) and a 1.5 second contact time. The effluent was analyzed by GLC using a 6 foot × ¼ inch column packed with Mole Sieve 13X/Porapak ® P from Alltech Associates, with a helium gas flow of 60 milliliters per minute and a column temperature of 25°–110° C. The results which are shown in Table I indicate catalyst activity to yield acrolein above 300° C., preferably about 400°–450° C. Although the propylene conversion increases with increased temperature (above 350° C.), the product selectivity decreases above about 450° C. The optimum reaction temperature appears to be about 400°–450° C.

TABLE I

| Reaction Temp., °C. | Air Oxidation of Propylene Using Mulled CuO/α-Al$_2$O$_3$ Catalyst | | |
|---|---|---|---|
| | % C$_3$ = Conversion | Acrolein m mol/min | % Selectivity |
| 200 | 0 | 0 | 0 |
| 250 | 0 | 0 | 0 |
| 300 | 0 | 0 | 0 |
| 350 | 0 | trace | trace |
| 400 | 5 | .007 | 35 |
| 450 | 15 | .013 | 22 |
| 500 | 20 | .012 | 15 |

EXAMPLE III

This example is a control illustrating catalyst activity wherein the CuO/α-Al$_2$O$_3$ catalyst was prepared by a calcining process. The procedure described in Example II was repeated with the exception that 10.72 grams (5 milliliters) of calcined CuO/α-Al$_2$O$_3$ catalyst prepared according to Example I was used. Although the propylene conversion increased with increasing reaction temperatures (e.g. 7% at 300° C., 12% at 400° C., and 50% at 500° C.), only a trace of acrolein product was found by GLC analysis of the product effluent.

EXAMPLE IV

This is a control run illustrating the catalyst activity of the α-Al$_2$O$_3$ support. The procedure described in Example II was repeated except 10 grams (5.8 milliliters) of α-Al$_2$O$_3$ was used as the catalyst. No acrolein product was obtained between 250° C. and 450° C. although the percent propylene conversion increased to 40%.

SUMMARY

Table II summarizes the invention wherein it is seen that mulled CuO/α-Al$_2$O$_3$ catalyst is an active catalyst for the air oxidation of propylene to acrolein but calcined CuO/α-Al$_2$O$_3$ catalyst and the α-Al$_2$O$_3$ support alone are not active catalysts for the air oxidation of propylene to acrolein.

TABLE II

| | | Summary of Data by GLC Air Oxidation of Propylene to Acrolein | | | | |
|---|---|---|---|---|---|---|
| | | Reaction Temperature | | | | |
| Example | Catalyst | 300° C. | 350° C. | 400° C. | 450° C. | 500° C. |
| | Invention: | | | | | |
| II | Mulled CuO/α-Al$_2$O$_3$* | | | | | |
| | a. % Propylene Conversion | trace | trace | 5 | 15 | 20 |
| | b. Acrolein, m mol/min | 0 | trace | .007 | .013 | .012 |
| | c. Acrolein, % Selectivity | 0 | trace | 35 | 22 | 15 |
| | Controls: | | | | | |
| III | Calcined CuO/α-Al$_2$O$_3$** | | | | | |
| | a. % Propylene Conversion | 7 | 2 | 12 | 24 | 50 |
| | b. Acrolein, m mol/min | 0 | 0 | 0 | trace | trace |
| | c. Acrolein, % Selectivity | 0 | 0 | 0 | trace | trace |
| IV | α-Al$_2$O$_3$ | | | | | |
| | a. % Propylene Conversion | 2 | 10 | 20 | 40 | — |
| | b. Acrolein, m mol/min | 0 | 0 | trace | 0 | — |

TABLE II-continued

| | | Summary of Data by GLC Air Oxidation of Propylene to Acrolein | | | | |
|---|---|---|---|---|---|---|
| | | Reaction Temperature | | | | |
| Example | Catalyst | 300° C. | 350° C. | 400° C. | 450° C. | 500° C. |
| | c. Acrolein, % Selectivity | 0 | 0 | trace | 0 | — |

*6.6 wt. % CuO on α-Al$_2$O$_3$ support
**1 wt. % CuO on α-Al$_2$O$_3$ support

I claim:

1. A method for preparing aldehyde from olefin comprising contacting said olefin with an oxygen containing gas at a temperature in the range of about 350° C. to about 500° C. in the presence of a catalyst produced by the method comprising (1) impregnating a support with an aqueous solution of cupric oxide, (2) subjecting the impregnated support to a temperature in the range of about 90° C. to about 150° C. for a time sufficient to produce a dry powder thereby providing a catalyst consisting essentially of a support impregnated with about 0.1 to about 5 weight percent cupric oxide.

2. A method of claim 1 wherein the support is -alumina.

3. A method of claim 1 or 2 wherein the aldehyde is acrolein and the olefin propylene.

4. A method of claim 1 or 2 wherein the aldehyde is methylcrolein and the oelfin isobutylene.

* * * * *